(12) United States Patent
Zhuang et al.

(10) Patent No.: US 6,586,344 B2
(45) Date of Patent: Jul. 1, 2003

(54) PRECURSORS FOR ZIRCONIUM AND HAFNIUM OXIDE THIN FILM DEPOSITION

(75) Inventors: Wei-Wei Zhuang, Vancouver, WA (US); David R. Evans, Beaverton, OR (US)

(73) Assignee: Sharp Laboratories of America, Inc., Camas, WA (US)

( * ) Notice: Subject to any disclaimer, the term of this patent is extended or adjusted under 35 U.S.C. 154(b) by 0 days.

(21) Appl. No.: 10/261,448

(22) Filed: Sep. 30, 2002

(65) Prior Publication Data

US 2003/0082927 A1 May 1, 2003

Related U.S. Application Data

(62) Division of application No. 10/020,471, filed on Oct. 30, 2001, now Pat. No. 6,472,337.

(51) Int. Cl.[7] .................................................. G01B 5/33
(52) U.S. Cl. ...................................................... 438/758
(58) Field of Search ................................ 438/758, 778, 438/785

(56) References Cited

U.S. PATENT DOCUMENTS

| | | | | |
|---|---|---|---|---|
| 4,982,019 A | * | 1/1991 | Purdy et al. | |
| 5,403,620 A | * | 4/1995 | Kaesz et al. | |
| 5,451,434 A | * | 9/1995 | Doellein | |
| 5,487,918 A | * | 1/1996 | Akhtar | |
| 5,496,597 A | * | 3/1996 | Soininen et al. | |
| 5,518,536 A | * | 5/1996 | Doellein | |
| 5,559,062 A | * | 9/1996 | Okabe et al. | |
| 5,908,947 A | * | 6/1999 | Vaartstra | |
| 6,060,755 A | * | 5/2000 | Ma et al. | |
| 6,090,992 A | * | 7/2000 | Wu et al. | |
| 6,159,855 A | * | 12/2000 | Vaartstra | |
| 6,207,589 B1 | * | 3/2001 | Ma et al. | |
| 6,297,539 B1 | * | 10/2001 | Ma et al. | |

FOREIGN PATENT DOCUMENTS

JP         2001214270         *   7/2001

OTHER PUBLICATIONS

E. Fredriksson, K. Forsgren, Thermodynamic modeling of MOCVD of ZrOsubA2 from Beta–diketonates and different oxygen sources, May 13, 1996, Elsevier Science S. A., pp. 256–263.*

B. Preauchat, S. Drawin, and S. Landals, Performances of a Microwave PECVD Reactor for Thin or Thick Oxide Coatings at Extremely High Deposition Rate, Dec. 1997, Society of Vaccum Coaters, 44th, 109–115.*

* cited by examiner

Primary Examiner—John F. Niebling
Assistant Examiner—Stanetta Isaac
(74) Attorney, Agent, or Firm—David C. Ripma; Matthew D. Rabdau; Scott C. Krieger

(57) ABSTRACT

A method of making a precursor for a thin film formed by chemical vapor deposition processes, includes mixing $ZCl_4$ with $H(tmhd)_3$ solvent and benzene to form a solution, where Z is an element taken from the group of elements consisting of hafnium and zirconium; refluxing the solution for twelve hours in an argon atmosphere; removing the solvents via vacuum, thereby producing a solid compound; and sublimating the compound at 200° C. in a near vacuum of 0.1 mmHg. A $ZO_x$ precursor, for use in a chemical vapor deposition process, includes a Z-containing compound taken from the group of compounds consisting of $ZCl(tmhd)_3$ and $ZCl_2(tmhd)_2$.

1 Claim, 2 Drawing Sheets

PRECURSORS FOR ZIRCONIUM AND HAFNIUM OXIDE THIN FILM DEPOSITION

CROSS-REFERENCE

This application is a divisional of application Ser. No. 10/020,471, filed Oct. 30, 2001, entitled "Precursors for Zirconium and Hafnium Oxide Thin Film Deposition," invented by Wei-Wei Zhuang, and David Russell Evans, now U.S. Pat. No. 6,472,337.

FIELD OF THE INVENTION

This invention relates to the synthesis of hafnium chloride alkoxides which can be used for the hafnium metal oxide thin film deposition via chemical vapor deposition (CVD) or atomic layer chemical vapor deposition (ALCVD) process.

BACKGROUND OF THE INVENTION

Currently, zirconium and hafnium precursors used for CVD or ALCVD are $HfCl_4$, $Hf(OR)_4$, where R=alkyl, such as $CH(CH_3)_2$, $Hf(tmhd)_4$, where tmhd=2,2,6,6-tetramethyl-3,5-heptanedionato, $Hf(tfac)_4$, where tfac=trifluoroacetylacetonate, and $Hf(NO_3)_4$, and similar precursors with zirconium components. For metal gate oxide applications, $HfCl_4$ has been reported as a potential source for a pure $HfO_2$ thin film deposition. Ryan C. Smith et al. *Chemical Vapor Deposition of the Oxides of Titanium, Zirconium and Hafnium for Use as High-k Materials in Microelectronic Devices. A Carbon-free Precursor for the Synthesis of Hafnium Dioxide*, Advanced Materials for Optics and Electronics 10, 105–114, 111–113 (2000).

As for the other precursors, $Hf(OR)_4$ is extremely air and moisture sensitive and is difficult to handle; $Hf(tmhd)_4$ is stable, but induces carbon contamination, which is difficult to remove; $Hf(tfac)_4$ is a volatile precursor, but its use includes a risk of fluorine contamination. There is no report about application of $Hf(NO_3)_4$ in ALCVD.

Because hafnium and zirconium have nearly identical electron configurations, they have nearly identical chemical properties. Thus, as is well know to those of ordinary skill in the art, they are virtually interchangeable in chemical compounds, and exhibit similar characteristics when used in semiconductor devices.

SUMMARY OF THE INVENTION

A method of making a precursor for a thin film formed by chemical vapor deposition processes, includes mixing $ZCl_4$ with $H(tmhd)_3$ solvent and benzene to form a solution, where Z is an element taken from the group of elements consisting of hafnium and zirconium; refluxing the solution for twelve hours in an argon atmosphere; removing the solvents via vacuum, thereby producing a solid compound; and sublimating the compound at 200° C. in a near vacuum of 0.1 mmHg.

A $ZO_x$ precursor, for use in a chemical vapor deposition process, includes a Z-containing compound taken from the group of compounds consisting of $ZCl(tmhd)_3$ and $ZCl_2(tmhd)_2$.

It is an object of the invention to provide hafnium precursors which may be used for the hafnium metal oxide thin film deposition via CVD or ALCVD process.

A further object of the invention is to reduce chlorine contamination while still providing a sufficiently volatile precursor.

Another object of the invention is to use alkoxide ligands to partially replace the chlorine, resulting in hafnium dichloride dialkoxide or hafnium chloride trialkoxide.

This summary and objectives of the invention are provided to enable quick comprehension of the nature of the invention. A more thorough understanding of the invention may be obtained by reference to the following detailed description of the preferred embodiment of the invention in connection with the drawings.

DETAILED DESCRIPTION OF THE PREFERRED EMBODIMENT

Figure 1:
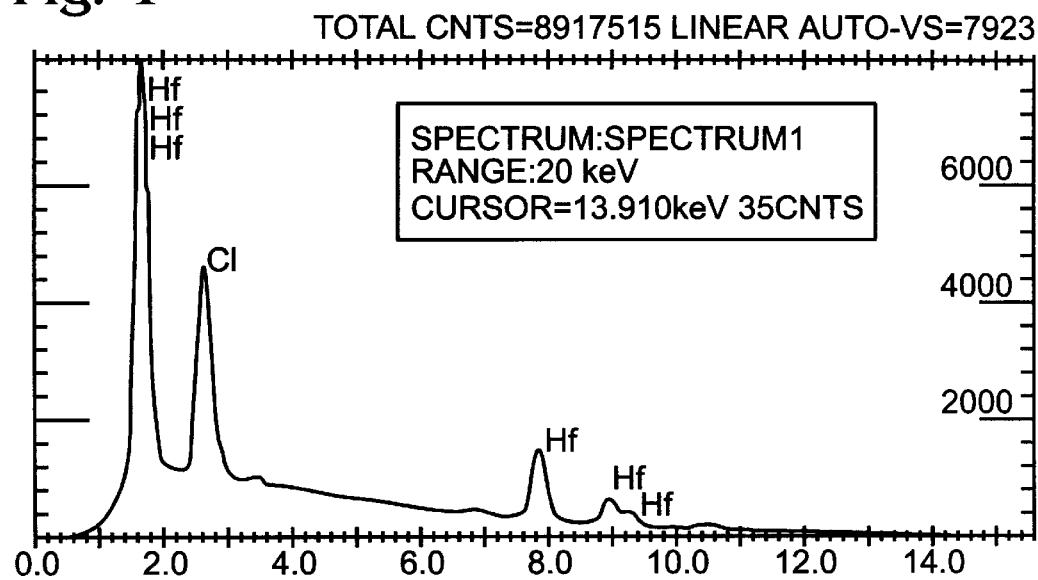
FIG. 1 depicts the EDS Spectra of $HfCl(tmhd)_3$.

As is well know to those of ordinary skill in the art, hafnium and zirconium have very similar chemical properties, and behave virtually identically when used in semiconductor devices. The examples herein use hafnium, but are also valid for zirconium-containing compounds and precursors.

Because $HfCl_4$ contains a very high concentration of chlorine, new hafnium precursors should contain less chlorine and have a higher volatility. To accomplish this, alkoxide ligands are used to partially replace the chlorine, resulting in hafnium dichloride dialkoxide or hafnium chloride trialkoxide. The compounds, $HfCl(tmhd)_3$ and $HfCl_2(tmhd)_2$, produce the desired results: chlorine is contained for the absorption requirement in atomic layer chemical vapor deposition (ALCVD) processes, and less chlorine is contained in the precursor, which reduces the chlorine contamination and provides higher volatility than that of $HfCl_4$.

The hafnium precursors of the method of the invention are $HfCl(tmhd)_3$ and $HfCl_2(tmhd)_2$, which contain chlorine to aid the absorption of molecules onto a wafer surface in ALCVD applications and which also contain less chlorine than $HfCl_4$, to reduce the chlorine contamination in hafnium metal oxide thin films.

The raw chemicals used for synthesis are $HfCl_4$, H(tmhd) and benzene solvent. $HfCl_4$, from Aldrich Chemical, was purified via sublimation. H(tmhd), from Strem Chemicals, was fractional distilled before use. Benzene was purified by reflux over benzophenone and sodium.

To make $HfCl(tmhd)_3$, $HfCl_4$ (50 g, 0.156 mol) was mixed with $H(tmhd)_3$ (86 g, 0.468 mol) in 600 mL benzene in a 1000 mL round bottom two-neck flask. The solution was strongly stirred after mixing. $HfCl_4$ gradually dissolved and the color of the solution was gradually changed to dilute yellow. The solution was refluxed for twelve hours in an argon atmosphere. The solvent was then removed via vacuum, and white solid compound was obtained. The compound was sublimated at 200° C. in a near vacuum of 0.1 mmHg, which produced 76.3 grams of purified HfCl(tmhd)$_3$, a 64% yield. The calculated composition for $HfClC_{33}H_{57}O_6$ is: Hf: 23.37%; C: 51.90%; Cl: 4.64%; H: 7.52%; and O: 12.57%. The actual analytical results indicate the following percentages: Hf: 24.42%; C: 51.89%; Cl: 4.71%; H: 7.62%; and O: 11.36%.

Likewise, in the synthesis of $HfCl_2(tmhd)_2$, $HfCl_4$ (50 g, 0.156 mol) was mixed with $H(tmhd)_3$ (58 g, 0.312 mol) in 600 mL benzene in a 1000 mL round bottom two-neck flask. The solution was strongly stirred after mixing. $HfCl_4$ gradually dissolved, and the color of the solution gradually changed to dilute yellow. The solution was refluxed for twelve hours under an argon atmosphere. Then the solvent was removed via vacuum and a white solid compound was obtained. The compound was then sublimed at 210° C. in a near vacuum of 0.1 mmHg, which produced 53 grams of purified $HfCl_2(tmhd)_2$, which is a yield of 55%. The calculated composition of $HfCl_2C_{22}H_{38}O_4$ is: Hf: 28.98%; C: 42.90%; Cl: 11.51%; H: 6.22%; and O: 10.39%. The actual analytical results indicated the following percentages: Hf: 30.24%; C: 43.13%; Cl: 11.67%; H: 6.24%; and O: 8.72%.

Figure 2:
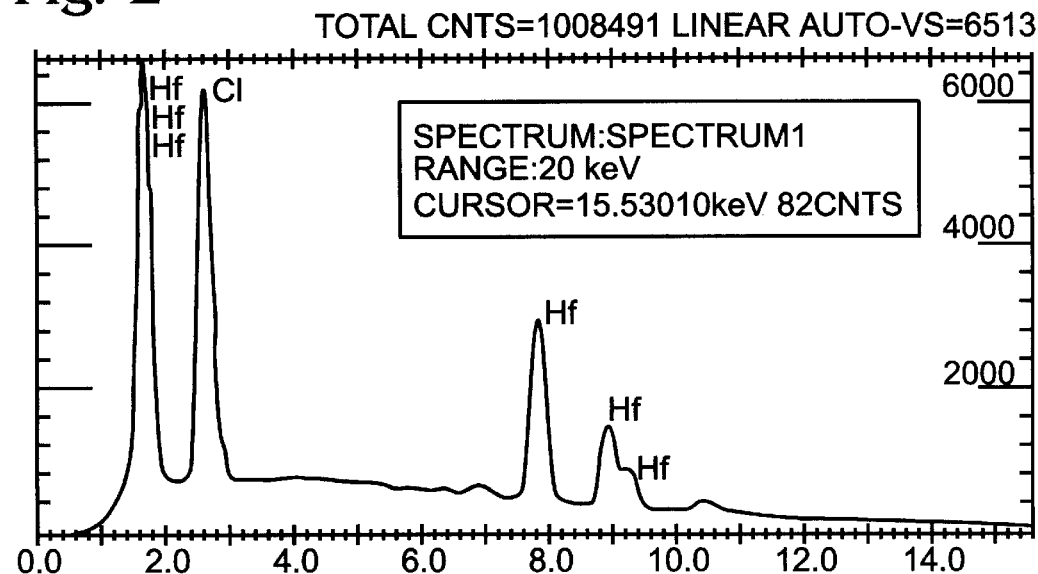
FIG. 2 depicts the EDS Spectra of $HfCl_2(tmhd)_2$.
Figure 3:
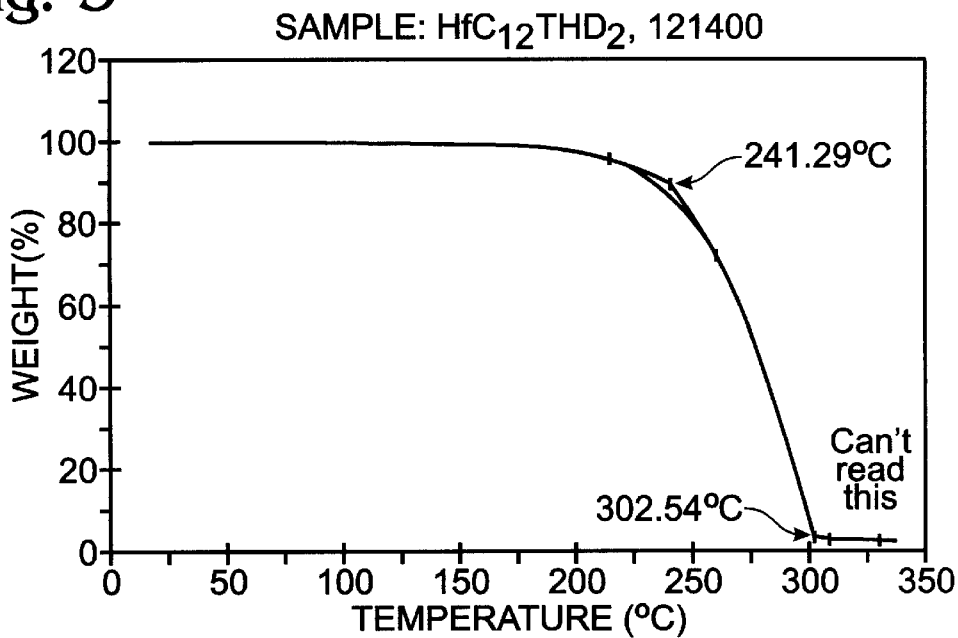
FIG. 3 depicts the TGA Spectra of $HfCl(tmhd)_3$.
Figure 4:
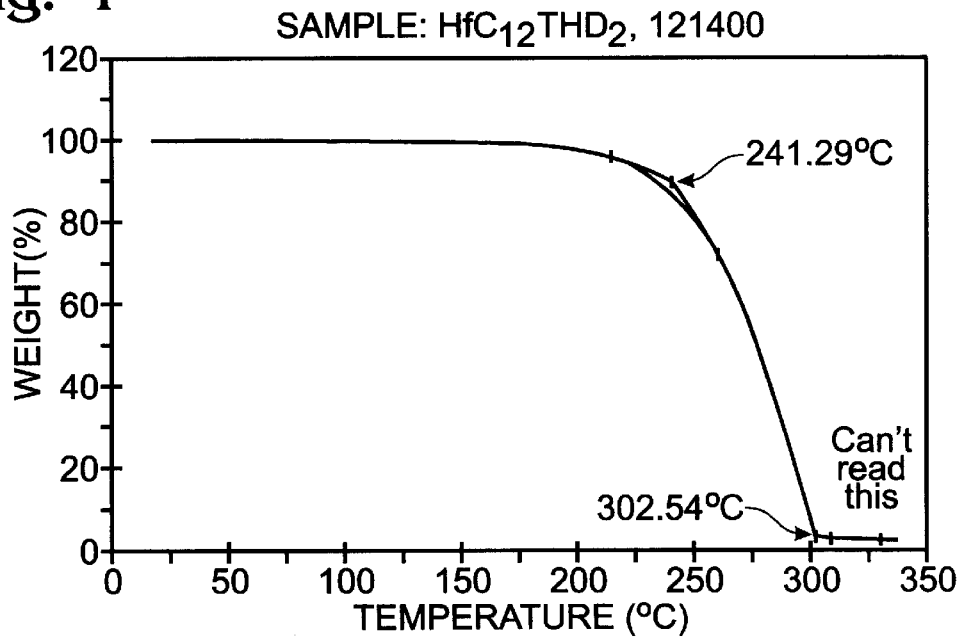
FIG. 4 depicts the TGA Spectra of $HfCl_2(tmhd)_2$.

The existence of chlorine in both precursors was further confirmed via EDS, as shown in FIGS. 1 and 2. The volatility of both compounds has been evaluated, via thermogravimetric analysis (TGA), as shown in FIGS. 3 and 4. The results indicate both new hafnium precursors are volatile and can be used as the sources for ALCVD applications.

The precursors may be used to from a $HfO_x$ thin film on a semiconductor device. A suitable substrate is prepared, which may include the formation of semiconductor structures thereon. The semiconductor structures may be masked to prevent deposition of the $HfO_x$ thin film in locations where the thin film is not required. The $HfO_x$ thin film may be deposited by CVD or ALCVD, after which, the mask is removed. The semiconductor device is then completed.

Because hafnium and zirconium have nearly identical electron configurations, they have nearly identical chemical properties. Thus, as is well know to those of ordinary skill in the art, they are virtually interchangeable in chemical compounds, and exhibit similar characteristics when used in semiconductor devices. The elements may be designated as "Z" in chemical formulae, where Z is an element taken from the group of elements consisting of hafnium and zirconium.

Thus, a method for compounding precursors for zirconium and hafnium oxide thin film deposition has been disclosed. It will be appreciated that further variations and modifications thereof may be made within the scope of the invention as defined in the appended claims.

We claim:

1. A $ZO_x$ precursor, where Z is an element taken from the group of elements consisting of hafnium and zirconium, for use in a chemical vapor deposition process, comprising:

a Z-containing compound taken from the group of compounds consisting of $ZCl(tmhd)_3$ and $ZCl_2(tmhd)_2$.

* * * * *